United States Patent [19]

Bier et al.

[11] Patent Number: 4,474,932

[45] Date of Patent: Oct. 2, 1984

[54] PROCESS FOR THE PRODUCTION OF AROMATIC ETHERS AND AROMATIC POLYETHERS

[75] Inventors: Gerhard Bier, Freiburg; Hans R. Kricheldorf, Hamburg, both of Fed. Rep. of Germany

[73] Assignee: Bayer Aktiengesellschaft, Leverkusen, Fed. Rep. of Germany

[21] Appl. No.: 475,709

[22] Filed: Mar. 16, 1983

[30] Foreign Application Priority Data

Mar. 27, 1982 [DE] Fed. Rep. of Germany ....... 3211421

[51] Int. Cl.³ .................................................. C08G 65/40
[52] U.S. Cl. ......................................... 528/25; 528/29; 528/86; 528/125; 528/126; 528/128; 528/174; 528/206; 528/207; 528/212; 528/214; 528/217; 528/219; 568/316; 568/631; 568/633; 568/635; 568/636

[58] Field of Search ................... 528/25, 86, 125, 126, 528/128, 174, 219, 206, 207, 29, 212; 260/607 AR; 568/316, 631, 633, 635, 636

[56] References Cited

U.S. PATENT DOCUMENTS

| | | | |
|---|---|---|---|
| 3,423,335 | 1/1969 | Phillips | 528/25 |
| 3,489,783 | 1/1970 | Shepard et al. | 528/25 |
| 3,502,710 | 3/1970 | Hatch | 528/86 |
| 3,761,449 | 9/1973 | Kaufman | 528/25 |
| 4,032,511 | 6/1977 | Blount | 528/25 |

*Primary Examiner*—Lester L. Lee
*Attorney, Agent, or Firm*—Connolly and Hutz

[57] ABSTRACT

Aromatic ethers or polyethers are produced by reacting aromatic fluorine compounds, in which one or more fluorine substituents are attached to an aromatic nucleus, with trialkyl silyl derivatives of phenols, in which one or more trialkyl silyl groups are attached to the residue of a mono- or polyphenol, or by reacting trialkyl silyl derivatives of fluorophenols with elimination of trialkylfluorosilane.

9 Claims, No Drawings

PROCESS FOR THE PRODUCTION OF AROMATIC ETHERS AND AROMATIC POLYETHERS

There are several known processes for attaching aromatic compounds through an ether bridge. Processes for the production of aromatic polyethers have only become known fairly recently, presumably because in formation of the polymer only high etherification yields lead to the high molecular weights necessary. Whereas yields of from 70 to 80% are satisfactory in the synthesis of low molecular weight compounds, yields of that order are not acceptable in the synthesis of high molecular weight compounds. Polyetherification is generally carried out by reacting an aromatic halide or dihalide with an aromatic phenolate or diphenolate (cf. U.S. Pat. Nos. 4,052,365, 4,169,178 and 4,105,635, British Pat. No. 1,348,630 and German Patent No. 1,545,106). If a reasonably complete reaction is to be obtained, it is necessary to use high-boiling solvents, such as tetramethyl sulfone, nitrobenzene. One disadvantage in this respect is that diphenolates generally differ in their solution behaviour from dihalides. The condensation reaction is promoted if the halide or dihalide contains a functional group which activates the halogen. Functional groups such as these are the sulfone group, the carbonyl group, the nitro group substituted in the o- or p-position, for example in the reaction of p,p'-dichlorodiphenyl sulfone with the bis-potassium salt of bisphenol A. According to German Offenlegungsschrifts Nos. 23 30 103 and 27 05 586, this reaction may be completed by using high-boiling polar dispersants, such as the cyclic aromatic sulfone ether corresponding to the following formula

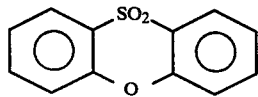

According to J. Pol. Sc. Al Vol. 5, p. 2375 (1967), difluorine compounds may also be used as the dihalogen compound where the dihalogen compound has the following structure

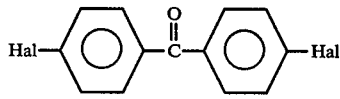

In known polyetherification processes, a salt, for example KCl or KF, is always formed as the cleavage product. However, this accumulation of salt increases the viscosity of the mixture and necessitates complicated purification processes. The use of high-boiling solvents leads to solutions of the polymers from which the polymers can only be isolated and purified with considerable effort in regard to the removal of high-boiling fractions and working-up of the large quantities of solvent.

Since aromatic polyethers show high thermal stability and favourable physico-chemical properties, there was a need to find a better and more simple process for their production which, in particular, facilitates condensation and its completion and does not involve the formation of any secondary products which are difficult to separate off.

The present invention relates to a process for the production of aromatic ethers and aromatic polyethers which is characterised in that an aromatic fluorine compound, in which one or more fluorine substituents are attached to an aromatic nucleus, are reacted at elevated temperature with a trialkyl silyl derivative of a phenol, in which one or more trialkyl silyl groups are attached to the residue of a mono- or polyphenol, with elimination of trialkyl fluorosilane.

The process according to the invention has the advantage that the volatile trialkyl fluorosilane formed escapes from the reaction vessel at the reaction temperature and that the polyether is obtained in a very high yield and in highly pure form after a comparatively short reaction time.

The reaction takes place in accordance with the following scheme:

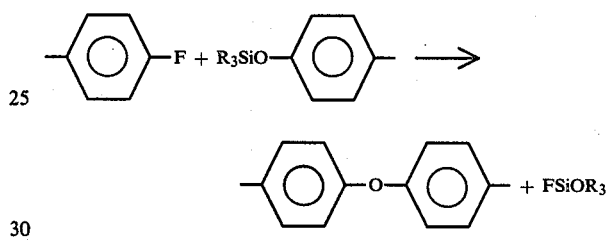

and is accompanied by the elimination of trialkyl fluorosilane from equivalent quantities of the fluorine substituents of the aromatic fluorine compounds and the trialkyl silyl groups of the trialkyl silyl derivatives of phenols.

In accordance with the reaction scheme, it is possible to use several groups of starting materials, namely monofluorine, difluorine or, optionally, polyfluorine derivatives of aromatic compounds, by reaction with mono- di- or poly-(trialkylsilyl)-derivatives of mono-, di- or polyphenols or aromatic compounds which contain one or more fluorine substituents and one or more trialkyl silyl groups in the same molecule. Monomeric ethers are formed where monofluorine derivatives of aromatic compounds are reacted with trialkyl derivatives of monophenols whereas bis-ethers, of which the production is preferred for certain purposes, are formed in the reaction of difluorine derivatives of aromatic compounds with trialkyl silyl derivatives of monophenols in a molar ratio of 1:2 and in the reaction of monofluorine derivatives of aromatic compounds with bis-(trialkylsilyl)-derivatives of diphenols.

All other reactions result in the formation of polyethers among which it is preferred to produce linear polyethers by reacting difluorine derivatives of aromatic compounds with bis-(trialkylsilyl)-derivatives of bisphenols and, optionally, by reacting the same or different monofluorine derivatives of trialkyl silyl derivatives of monophenols.

It is less preferred to produce branched or crosslinked polyethers by reacting trifluorine derivatives of aromatic compounds with tris-(trialkylsilyl)-derivatives of triphenols or by adding trifunctional starting materials of the type in question to the above-mentioned difunctional or monofunctional starting materials.

Suitable trialkyl silyl derivatives of phenols are those containing from 1 to 10 carbon atoms in the alkyl radical, preferably containing from 1 to 3 carbon atoms in the alkyl radical and, more preferably, the trimethyl silyl derivatives. The fluorine derivatives of aromatic compounds and the trialkyl silyl derivatives of phenols preferably contain 2 aromatic nuclei in the molecule, although starting materials containing 1 aromatic nucleus may also be used. Reactants or mixtures of starting materials differing in the structure of the aromatic nuclei are suitable.

It is also preferred for the reactive substituents in starting materials containing 2 aromatic nuclei, namely the two fluorine substituents, the two trialkyl silyl groups or a fluorine substituent and a trialkyl silyl group, to be attached to different aromatic nuclei. In addition, a symmetrical structure of the molecules, for example with the reactive substituents in the 4,4'-position of the binuclear aromatic compounds and diphenols, is frequently preferred, although other positions are also possible.

Particularly reactive or suitable and therefore preferred aromatic fluorine compounds are those which contain an activating group, such as a sulfone group, a keto group, a —CO₂R-group, a phenyl group or a nitro group in the o- or p-position.

The following are examples of the difluorine compounds:

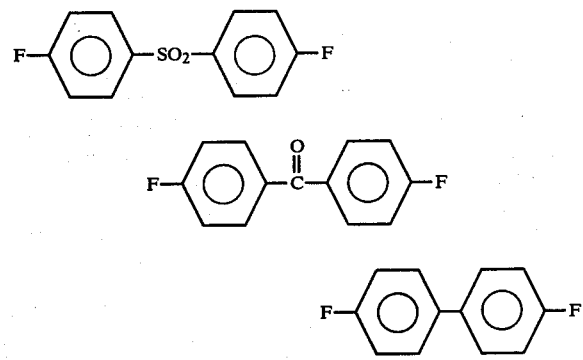

The following are examples of the trialkyl-Si-derivatives of phenols and diphenols:

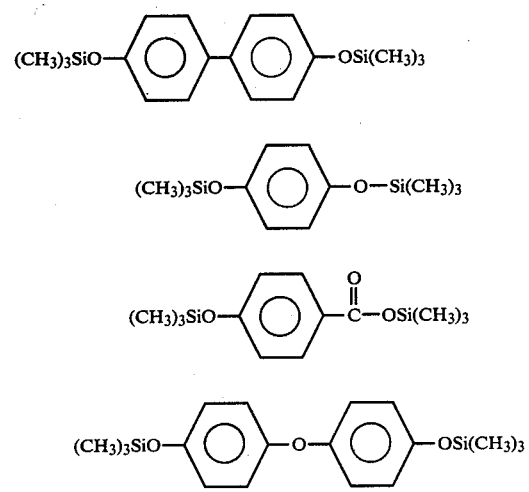

-continued

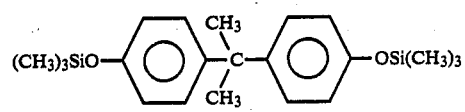

It is also possible to use compounds which contain the fluorine and the trialkyl-Si-group in one and the same molecule, for example

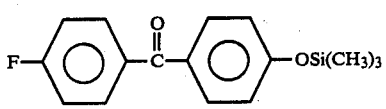

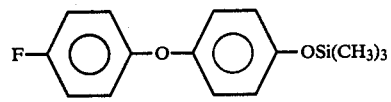

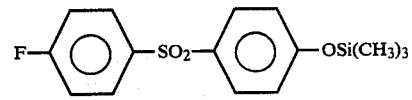

The fluorine compounds may be obtained in known manner from the corresponding aromatic compounds. The trialkyl silyl derivatives of phenols may readily be obtained by reacting trialkyl halogen silane with alkali phenolates or by reacting the free phenols with trialkyl chlorosilane/triethylamine and with hexamethyl disilazane and other N-trialkyl silyl/nitrogen compounds. Fluorine-substituted phenols are silylated with trialkyl chlorosilane/triethylamine or are obtained in the form of the alkali salts using trialkyl chlorosilane.

The particular advantage of the process according to the invention lies in the particular ease with which the melt condensation reaction can be carried out. Accordingly, it is preferred above all to carry out the process according to the invention as melt condensation in the absence of solvents. The condensation reaction may also be carried out in high-boiling solvents, including inter alia nitrobenzene and tetramethyl sulfone. There is generally no need for the polyethers to be purified, although they may be subjected to dissolution and reprecipitation, for example to enable physico-chemical measurements to be carried out on highly pure products.

The reaction temperature is generally in the range from 150° to 350° C. and preferably in the range from 170° to 350° C. In this connection, trialkyl fluorosilane is first split off and removed at temperatures in the range from 170° to 270° C., after which the temperature is increased to complete the elimination of trialkyl fluorosilane and the condensation process.

Surprisingly, the ethers and polyethers are obtained in very high yields ranging from 96 to more than 98% and also in highly pure form. Highly polymeric polyethers are surprisingly obtained in reaction times of only 2.5 to 3.5 hours. The pressure may be between 0.3 and about 2 bars. The reaction is preferably carried out at normal pressure or under a slight reduced pressure. The reaction vessel is best provided with means for condensing the trialkyl fluorosilane which is re-used for the reaction with alkali phenolate.

The reaction is preferably carried out in the presence of a catalyst from the class of fluoride salts, such as ammonium fluoride or one of the alkali fluorides, particularly KF, RbF or CsF. The catalyst is best used in a quantity of from 0.1 to 10 mg per g of starting materials.

The degree of condensation may be influenced within very wide limits through the choice of the starting materials and the reaction conditions. In the production of oligomeric compounds for example, the polycondensation reaction may be stopped on reaching certain average degress of condensation and the terminal groups may optionally be closed by means of calculated quantities of monofluorine derivatives of aromatic compounds or trialkyl silyl derivatives of monophenols. The process is particularly suitable for the production of block polymers in which the individual blocks emanate from monomers of different structure. In this way, it is possible for example to attach polyaryl esters or polyaryl ketones to polyaryl ethers, to link polyaryl ethers differing from one another in the structure of the aromatic nuclei or to join together recurring sections of polyaryl sulfones and polyaryl ethers. By further reaction with trifunctional starting materials, it is possible to increase molecular weight even further and to crosslink or harden oligomers or high polymers.

The products may be used in the lacquer field and for coatings, but above all as high polymers for the production of fibres, filaments and mouldings.

The products show high thermal stability. Using dried samples of the products of Examples 1 and 2, it was found by thermographic analysis at a heating rate of 8° K./minute that up to 380° C. there is no weight loss, up to 430° C. there is a weight loss of 1% by weight and up to 444° C. a weight loss of 2% by weight. The samples are thermally stable at a temperature of up to about 450° C. and only begin to undergo exothermic decomposition at upwards of about 560° C.

EXAMPLE 1

37.1 g (0.1 mole) of bis-trimethyl silyl-bisphenol A and 25.4 g (0.1 mole) of 4,4'-bis-fluorophenyl sulfone are heated together with 50 mg of potassium fluoride to a temperature of 270° C. in a gentle stream of nitrogen, a vigorous evolution of trimethyl fluorosilane beginning within a period of 10 minutes. The melt which has become viscous after 30 minutes is heated for 2.5 hours to 320° C. The evolution of trimethyl fluorosilane comes to a stop and filaments can be drawn from the highly viscous melt. Dissolution in methylene chloride and precipitation with methanol gives a white, fibrous polymer (in a yield of 97%) which is found by vapour pressure osmometry to have an average molecular weight (number average) of from 8500 to 9500. The polymer has an inherent viscosity $\eta_{inh}$ of from 0.7 to 0.8, as measured in tetrachloroethane at 20° C. (c=2 g/l).

EXAMPLE 2

37.1 g (0.1 mole) of bis-trimethyl silyl-bisphenol A and 25.4 g (0.1 mole) of 4,4'-bis-fluorophenyl sulfone are heated together with 50 mg of caesium fluoride to 170° C. in a gentle stream of nitrogen, a vigorous evolution of trimethyl fluorosilane being initiated. After 30 minutes, the temperature is increased to 320° C. for 2.5 hours and the polymer precipitated with methanol from a solution of methylene chloride. The yield of white polymer amounts to 98%. The polymer has an inherent viscosity of 1.4 dl/g, as measured in tetrachloroethane (c=2 g/l).

EXAMPLE 3

39.4 g (0.1 mole) of bis-trimethyl silyl-4,4'-dihydroxy diphenyl sulfone, 25.4 g (0.1 mole) of 4,4'-bis-fluorophenyl sulfone and 50 mg of caesum fluoride are heated to 270° C., after which a vigorous evolution of trimethyl fluorosilane commences. After 30 minutes, the reaction mixture is heated to 340° C. for 2.5 hours and the product precipitated with methanol from a solution of tetrachloroethane. Yield: 97% of a white, fibrous polymer. Vapour pressure osmosis in tetrachloroethane reveals an Mn value of 16,000.

EXAMPLE 4.

28.2 g (0.1 mole) of bis-trimethyl silyl-4-hydroxy benzoic acid, 25.4 g (0.1 mole) of 4,4'-bis-fluorophenyl sulfone and 50 mg of caesium fluoride are heated to 270° C., trimethyl fluorosilane being given off. After 1 hour, the melt is heated to 320° C., followed after 2 hours by dissolution in tetrachloroethane and precipitation with methanol. Yield: 96% of a yellowish, fibrous polymer.

EXAMPLE 5

37.1 g (0.1 mole) of bis-trimethyl silyl/bisphenol A, 21.8 g (0.1 mole) of 4,4'-difluorobenzophenone and 50 mg of caesium fluoride are heated for 1 hour to 300° C. with elimination of trimethyl fluorosilane. The viscous melt formed is subjected to condensation for 2 hours at 320° C. Dissolution in tetrachloroethane and precipitation with methanol gives a white, fibrous product in a yield of 96%.

EXAMPLE 6

33.0 g (0.1 mole) of bis-trimethyl silyl-4,4'-dihydroxy diphenyl, 21.8 g (0.1 mole) of 4,4'-difluorobenzophenone and 50 mg of CsF are heated to 300° C. in a gentle stream of nitrogen with elimination of trimethyl fluorosilane. After 2 hours, the temperature is increased to 330° C. for another 2 hours, the contents of the flask solidifying. Since the polyether ketone does not have a melting point up to 420° C. and decomposes at higher temperatures, it is mechanically size-reduced in the cold and washed with boiling methylene chloride. The light brown product was obtained in a yield of 94%.

The product is soluble inter alia in methylene chloride, tetrachloroethane, dimethyl sulfoxide, dimethyl formamide/5% LiCl and trifluoroacetic acid. Production of the starting materials:

EXAMPLE A 228 g (1 mole) of bisphenol A and 400 g (approximately 2.5 moles) of hexamethyl disilazane are heated under reflux until the evolution of ammonia comes to a stop. The excess hexamethyl disilazane is then removed in vacuo and the bis-trimethyl silyl/bisphenol A concentrated by distillation in vacuo. Yield 98%.

EXAMPLE B 228 g (1 mole) of bisphenol A and 220 g (2 moles) of trimethyl chlorosilane are dissolved in 2.5 liters of dry toluene and 209 g (2 moles) of triethylamine added dropwise to the resulting solution with heating and vigorous stirring. The reaction mixture is then refluxed for 20 minutes, cooled to 10°-20° C., rapidly filtered and the bis-trimethyl silyl/bisphenol A isolated from the filtrate by distillation in vacuo. Yield 91%.

EXAMPLE C 119 g (0.5 mole) of the sodium salt of 4-fluoro-4'-hydroxy benzphenol are suspended in 500 ml of dry tetrahydrofuran (or dioxane, acetonitrile) and the resulting suspension heated to reflux temperature. 0.5 mole of trimethyl chlorosilane is then rapidly added dropwise with stirring, after which the reaction mixture is refluxed for 20 minutes. The solvent is distilled off and the product isolated by distillation in vacuo. Yield 91%.

We claim:

1. A process for the production of an aromatic ether or an aromatic polyether wherein an aromatic fluorine compound, in which one or more fluorine substituents are attached to an aromatic nucleus, is reacted at a temperature of from 150° to 350° C. with an equimolar amount of a trialkyl silyl derivative of a phenol, in which one or more trialkyl silyl groups are attached to the residue of a mono- or polyphenol, with elimination of trialkyl fluorosilane.

2. A process as claimed in claim 1, wherein the trialkyl silyl derivative of a phenol is the trimethyl silyl derivative.

3. A process as claimed in claim 1, wherein the aromatic fluorine compound is an aromatic difluorine compound and the trialkyl silyl derivative of a phenol is a bis-trialkyl silyl derivative of a diphenol.

4. A process as claimed in claim 1, wherein the aromatic fluorine compound is the trialkyl silyl derivative of a fluorophenol.

5. A process as claimed in claim 4, wherein the fluorine substituents and/or trialkyl silyl groups are attached to different aromatic nuclei.

6. A process as claimed in claim 1, wherein a catalytically-active inorganic fluorine compound of the ammonium fluoride or alkali fluoride type is added.

7. A process as claimed in claim 6, wherein the catalytically-active inorganic fluorine compound is potassium, nibidium or caesium fluoride in an amount of from 0.1 to 10 mg per g of starting materials.

8. A process as claimed in claim 1 wherein the reaction is carried out in the melt or in the presence of a high-boiling solvent.

9. A process as claimed in claim 1 wherein the aromatic fluorine compound has the fluorine substituent activated by an activating group comprising a sulfo, nitro, keto, phenyl or —COOR which is ortho or para to the fluorine.

* * * * *